US011478177B2

(12) United States Patent
Yuen (10) Patent No.: US 11,478,177 B2
(45) Date of Patent: Oct. 25, 2022

(54) PHYSIOLOGICAL SIGNAL COLLECTION APPARATUS AND PERFORMANCE MONITORING APPARATUS INCORPORATING SAME

(71) Applicant: Dayton Technologies Limited, Hong Kong (HK)

(72) Inventor: Paul Anthony Yuen, Hong Kong (HK)

(73) Assignee: Dayton Technologies Limited, Hong Kong (HK)

( * ) Notice: Subject to any disclaimer, the term of this patent is extended or adjusted under 35 U.S.C. 154(b) by 1145 days.

(21) Appl. No.: 15/846,173

(22) Filed: Dec. 18, 2017

(65) Prior Publication Data
US 2018/0116544 A1 May 3, 2018

Related U.S. Application Data

(63) Continuation-in-part of application No. 13/520,862, filed as application No. PCT/IB2011/050078 on Jan. 10, 2011, now abandoned.

(30) Foreign Application Priority Data

Jan. 8, 2010 (HK) ................................ 10100226.4

(51) Int. Cl.
*A61B 5/00* (2006.01)
*A61B 5/24* (2021.01)
(Continued)

(52) U.S. Cl.
CPC ............ *A61B 5/282* (2021.01); *A61B 5/1123* (2013.01); *A61B 5/6823* (2013.01);
(Continued)

(58) Field of Classification Search
CPC ......... A61B 5/256; A61B 5/257; A61B 5/251; A61B 5/254; A61B 5/28; A61B 2560/0412; A61B 5/6831; A61B 5/683; A61B 5/02438; A61B 5/0245; A61B 5/308; A61B 5/282; A61B 5/1123; A61B 5/6823;
(Continued)

(56) References Cited

U.S. PATENT DOCUMENTS 3,834,373 A * 9/1974 Sato .................... A61B 5/25
  252/514
2002/0019166 A1* 2/2002 Ubby .................... A61B 5/282
  439/505

(Continued)

*Primary Examiner* — Eun Hwa Kim
*Assistant Examiner* — Adam Z Minchella (57) ABSTRACT

A physiological signal collection electrode comprises a signal collection pad having a skin contact portion, a signal output pad and an elongate bridging portion interconnecting the signal collection pad and the signal output pad. The signal collection pad, the signal output portion and the bridging portion are integrally molded of a flexible, conductive and resilient material. The width of the bridging portion is substantially smaller than that of the skin contact portion. A narrowed bridging portion operates to concentrate collected physiological signals collected by the skin contact portion before the signals are output to the signal output pad. An elongate bridging portion reduces skin covering area for better wearer comfort as well as providing better resiliency to the electrode when the bridging portion is extended.

20 Claims, 7 Drawing Sheets

(51) Int. Cl.
*A61B 5/282* (2021.01)
*A61B 5/11* (2006.01)
*A61B 5/316* (2021.01)

(52) U.S. Cl.
CPC ............ *A61B 5/6831* (2013.01); *A61B 5/316* (2021.01); *A61B 2503/10* (2013.01); *A61B 2560/0412* (2013.01); *A61B 2562/0219* (2013.01); *A61B 2562/164* (2013.01); *A61B 2562/18* (2013.01)

(58) Field of Classification Search
CPC ................ A61B 5/316; A61B 2503/10; A61B 2562/0219; A61B 2562/164; A61B 2562/18
See application file for complete search history.

(56) References Cited

U.S. PATENT DOCUMENTS

| | | | | |
|---|---|---|---|---|
| 2002/0019586 | A1* | 2/2002 | Teller | A61B 5/02055 128/903 |
| 2005/0239075 | A1* | 10/2005 | Yanagidaira | B62D 1/06 435/6.16 |
| 2006/0094948 | A1* | 5/2006 | Gough | A61N 1/0484 600/372 |
| 2007/0012089 | A1* | 1/2007 | Stasz | G01F 1/00 73/31.01 |
| 2007/0225611 | A1* | 9/2007 | Kumar | A61B 5/25 600/523 |
| 2007/0285868 | A1* | 12/2007 | Lindberg | A61B 5/0245 600/382 |
| 2009/0099473 | A1* | 4/2009 | Dunseath | A61B 5/291 600/544 |
| 2010/0317958 | A1* | 12/2010 | Beck | A61B 5/316 600/391 |
| 2011/0259638 | A1* | 10/2011 | Sherrill | D04B 1/14 174/70 R |
| 2014/0336493 | A1* | 11/2014 | Kulach | A61B 5/6831 600/390 |
| 2014/0364716 | A1* | 12/2014 | Smink | A61B 5/6805 600/393 |

* cited by examiner

PHYSIOLOGICAL SIGNAL COLLECTION APPARATUS AND PERFORMANCE MONITORING APPARATUS INCORPORATING SAME

CROSS-REFERENCE TO RELATED APPLICATIONS

This application is a continuation-in-part application of application Ser. No. 13/520,862, which is the National Stage of International Application No. PCT/IB2011/50078 filled Jan. 1, 2007.

The present invention relates to physiological signal collection apparatus, and more particularly to chest-worn physiological signal collection apparatus. This invention also relates to performance monitoring apparatus comprising a physiological signal collector and a signal processing device for processing collected physiological signals. More specifically, although not solely limited thereto, the present invention also relates to chest-worn swim monitors.

Physiological signal collectors are useful for collecting physiological data of a person during physical exercises, during medical examination or during everyday life. Typical physiological signals which are commonly collected for processing and analyzing include ECG, heart rate, blood pressure, blood oxygen content, body temperature. The collected signals are typically processed and converted into data which provide information on the state of health, physical fitness, or physical performance of a person.

A chest strap is a known type of physiological signal collectors adapted to be chest-worn by a person for collecting physiological signals during physical exercises or activities. Physiological signals commonly collected by a chest strap include, for example, heart-rate, ECG pulses, skin conductivity, infra-red absorption or other electrical or opto-electrical signals measureable from the skin of a person.

A typical chest strap usually includes a plurality of electrodes or sensors which is mounted on a flexible plastic chest strap in a spaced apart manner to collect weak physiological signals in electrical or optical form from a human body for differential signal processing. Each electrode typically comprises a signal reception pad having a signal reception surface with a surface area large enough to collect signals which are strong enough for processing by a signal processing device, such as a heart rate signal processor.

The flexible plastic strap is usually a pre-assembled strap loop which comprises a length adjustment or tension adjustment arrangement to tighten the strap against the body of a person, usually the chest, during use to provide electrical contact between the electrodes and the skin of a user. The strap is usually made of soft plastics to provide flexibility for body wearing and electrical insulation between the electrodes. The tensions adjustment arrangement typically comprises a length of soft plastic strap portion which runs around buckle or clasp arrangements.

However, such chest-type physiological data collectors are uncomfortable and difficult to wear and adjust. Also, it is noted that known chest straps do not operate well enough for wet applications, for example swimming or water sports.

Therefore, it would be advantageous to provide improvement chest straps to mitigate shortcoming aspects of conventional chest straps.

DISCLOSURE

According to the disclosure, there is provided a physiological signal collection electrode comprising a signal collection pad having a skin contact portion, a signal output pad, and an elongate bridging portion interconnecting the signal collection pad and the signal output pad, wherein the signal collection pad, the signal output portion and the bridging portion are integrally molded of a flexible, conductive and resilient material; characterized in that the width of the bridging portion is smaller than that of the skin contact portion.

A narrowed bridging portion operates to concentrate collected physiological signals collected by the skin contact portion before the signals are output to the signal output pad. An elongate bridging portion reduces skin covering area for better wearer comfort as well as providing better resiliency to the electrode when the bridging portion is extended. The signal collection pad coupled with the narrowed bridging portion makes the electrode more flexible and is therefore particularly suitable for collecting human ECG signals, for example, from rib cage regions of a person.

To mitigate spurious signals reception of the bridging portion, the bridging portion may be covered by a flexible, resilient and waterproof insulating material such as rubber, silicone rubber or soft plastics. The insulating material is preferably over-molded on the electrode for better shielding against spurious signals.

The skin contact portion may elevate from the signal collection pad and may be surrounded by an insulating material. The surface of the insulating material is preferably flush with the surface of the skin contact portion, thereby making a continuous flush surface for better wear comfort while maintaining a well-defined signal collection area.

The signal output pad may include a signal output terminal to output the collected physiological signal for external processing.

The effective resistance of the electrode measured between the skin contact portion and the signal output terminal is less than 1 k$\Omega$, preferably less than 500$\Omega$, and more preferably less than 400$\Omega$. It has been found that such a low resistance is beneficial for in or under water applications. Accordingly, the electrode may be configured as an ECG signal collector for collecting ECG signals during swimming.

The skin contact surface may be flexible and elongate with an effective skin contact surface of between 7.5 cm$^2$ to 20 cm$^2$.

The skin contact portion may be between 1.5-2.5 cm wide and 5-8 cm long.

The narrowed bridging portion may be between 6 and 10 cm long and about half or less than half of the width of the skin contact portion.

The flexible, conductive and resilient material may be selected form carbonized rubber, carbonized fabrics, Nickel copper plated polyester, silver nylon mesh, cotton silver bamboo fiber, or other conductive fabrics such as metalized fabrics or the like.

According to another aspect of the present invention, there is provided an ECG signal collection strap comprising first and second ECG signal collection electrodes which are respectively mounted at first and second free longitudinal ends of an insulating strap, wherein each signal collection electrode comprises a signal output terminal and a signal collection pad having a skin contact surface which is adapted for collecting ECG signals from the skin of a user, characterized in that, the ECG signal collection electrode is an electrode of the present invention.

According to yet another aspect of the present invention, there is provided an ECG signal collection strap comprising first and second ECG signal collection electrodes which are respectively mounted at first and second free longitudinal ends of an insulating strap, wherein each signal collection electrode comprises a signal output terminal and a signal collection pad having a skin contact surface which is adapted for collecting ECG signals from the skin of a user, characterized in that, first and second mechanical fastening parts are provided respectively at the first and second longitudinal ends of the strap for converting the longitudinal strap into a strap loop for wearing on the body of a user, and the first and second mechanical fastening parts are arranged such that the strap will urge the skin contact surfaces of the first and second electrodes to abut skin of the user to make electrical contacts and to collect physiological signals when the strap loop is worn on the body of the user with the fastening parts engaged.

Such an arrangement facilitates front wearing of the strap as a user could engage the fastening parts at the front of the chest.

The signal output terminal comprises a mechanical mating portion of a conductive mechanical fastening part which is adapted for engagement with a complementary mechanical mating portion of a counterpart mechanical fastening part. A signal output terminal which is also a mechanical portion of a conductive mechanical fastening part means added user convenience because a user only needs to make a single connection step to achieve both electrical and mechanical connection.

The first and second mechanical fastening parts of the signal collection strap may be adapted for mechanical engagement with a portable ECG signal processing device, and to form a complete strap loop upon engagement with the portable ECG signal processing device, and wherein the strap is arranged such that ECG signals collected by the electrodes are delivered to the portable ECG signal processing device via the mechanical fastening parts. The portable ECG signal processing device is useful for ECG signal processing as well as serves as a latching bridging for converting the strap into a strap loop.

The signal output terminal may also a conductive mating portion of a snap fastener part. This facilitates snap fastening for making both electrical and mechanical connections for added convenience.

The insulating strap may be elastic and its length may be adjustable. The insulating strap may be made of air and/or moisture permeable elastomeric fabric such as elastomeric polyamide or swimwear fabric such as Nylon, Lycra®, polyester, or the like. Anti-slid texture may be formed on portions of the insulating strap which are in contact with user skin during use.

The bridging portion of each of the electrodes may be embedded within the insulated strap. The signal collection pad of each of the electrodes may be bonded on the insulated strap.

The mechanical fastening components may be arranged to convert the longitudinal tensioning strap into a tensioning strap loop The conductive parts of the mechanical fastening components may form part of the signal output terminals and/or vice versa.

The swim motion detector and the ECG signal processing device may be formed as a module and may be housed within a common housing, and the ECG signal processing device has first and second signal input terminals. The ECG signal processing device may be arranged to obtain ECG signals from the strap via the signal output terminals of the strap.

The swim motion detector may comprise a 3-axis accelerometer which is arranged to collect swim motion data.

The effective signal path resistance between the skin contact portion of the electrode and a corresponding output terminal may be less than that of the swim water signal path between the skin in contact with the electrode and the corresponding output terminal.

The monitor is adapted for use in sea water, chlorinated water or other ionized water, and the effective signal path resistance of each of the electrodes is below 800 ohms, preferably below 500 ohms.

Each of the first and second terminals of the ECG processing device may be formed as a mating portion of a mechanical fastener part, and each of the output terminals of the strap is formed into a complementary mating portion of a counterpart mechanical fastener part.

The physiological signal processing module may connect with the signal collection strap to form a complete strap loop when they are mechanically engaged.

The strap loop is a body strap such as a chest strap, head strap, arm strap, thigh strap, or the like.

A physiological signal collection electrode for collecting ECG signals is disclosed herein. The signal collection electrode comprises a signal collection portion comprising a signal collection pad, a signal output portion comprising a signal output pad and a signal transmission portion interconnecting the signal collection portion and the signal output portion and comprising a signal transmission pad; wherein the signal collection pad, the signal output pad, and the signal transmission pad are integrally formed of a flexible, conductive and resilient material to form an electrode main body.

The signal collection pad comprises a signal collection surface, and the signal output pad comprises a signal output surface; wherein the signal transmission pad is sealed watertight by an insulating material which is flexible, resilient and water impervious.

The electrode has a resistance between the signal collection surface and the signal output pad and the resistance is adapted to enable collection of ECG signals in chlorinated water or sea water.

The electrode main body may have a resistance of 400 ohm or less between the signal collection surface and the signal output surface.

The flexible, conductive and resilient material may be selected from a group consisting of carbonized elastomer, including carbonized rubber, carbonized silicone rubber, and carbonized thermoplastics; and the insulating material is a non-conductive thermoplastic elastomer, including rubber and soft plastics.

The insulating material may be over-molded on the signal transmission pad by thermal over-molding or other laminating process.

The signal collection pad except the signal collection surface, the signal output pad except the signal output surface, and the signal transmission pad are waterproof sealed by the insulating material.

The insulating material may be over-molded on the electrode main body to form an insulating and waterproof integral sealing sleeve; wherein the electrode main body comprises an inward facing side on one side of the electrode main body on which side the signal collection surface and the signal output surface are defined, an outward facing side which is on another side of the electrode main body and faces away from the inward facing side, and a peripheral side interconnecting the inward facing side and the outward facing side; and wherein the integral sealing sleeve includes a peripheral portion which wraps around and laminates the peripheral side of the electrode main body to make the peripheral side waterproof.

The electrode main body is elongate and extends along a longitudinal axis, the signal transmission pad is substantially narrower than the signal collection pad, and the signal collection pad follows a tapering profile to taper to narrow towards a first longitudinal end to join the signal transmission pad at the first longitudinal end; and wherein the peripheral portion of the integral sealing sleeve has an exterior lateral boundary which follows the tapering profile of the signal collection pad.

The signal transmission pad may have a substantially higher per-unit-length resistance than the signal collection pad in a longitudinal direction of the longitudinal axis.

The per-unit-length resistance of the signal transmission pad in the longitudinal direction may be more than two times or three times the per-unit-length resistance of the signal collection portion in the longitudinal direction.

The signal collection portion may curve in a first curvature to taper to narrow on extending towards the signal transmission portion and curves in a second curvature opposite to the first curvature to merge smoothly with the signal transmission portion at the first longitudinal end.

The signal collection pad may comprise a skin contact pad having a peripheral wall which extends around the signal collection surface, wherein the peripheral wall displaces the signal collection surface inwardly along an axial direction with respect to the signal transmission pad, connects the signal collection surface to the signal transmission pad, and defines a height of the signal collection surface with respect to the signal transmission pad; and wherein the peripheral wall curves in a first curvature to taper to narrow and then curves in a second curvature opposite to the first curvature to smoothly merge with the signal transmission pad at the first longitudinal end.

The electrode main body is elongate and may extend along a longitudinal axis and has a substantially uniform thickness; and wherein the signal transmission portion is substantially narrower than the signal collection portion and the signal output portion.

The signal collection pad may comprise a flange portion which extends radially away from an outward end of the peripheral wall and surrounds the outward end; and wherein the flange portion is peripherally sealed by a watertight lamination formed by the integral sealing sleeve and the peripheral wall and the signal collection surface of the signal collection pad protrude inwardly with respect to the sleeve.

The skin contact pad may have a first longitudinal end portion comprising a first longitudinal end which is proximal to and in abutment with the signal transmission pad, and a second longitudinal end portion comprising a second longitudinal end which is distal to the signal transmission portion; wherein the flange portion comprises a distal longitudinal end portion which extends along the second longitudinal end portion of the skin contact pad, the distal longitudinal end portion being a longitudinal end which is distal to the signal transmission portion; and wherein the integral sealing sleeve comprises a free longitudinal end portion which extends along the distal longitudinal end portion of the flange portion, wraps around the distal longitudinal end portion of the flange portion and forms a waterproof lamination on the distal longitudinal end portion of the flange portion.

The second longitudinal end portion of the skin contact pad may have a rounded exterior periphery. The distal longitudinal end portion of the flange portion surrounding the second longitudinal end portion of the skin contact pad may have a rounded exterior periphery having a substantially uniform radial extent from the rounded exterior periphery of the second longitudinal end portion of the contact pad. The free longitudinal end portion of the integral sealing sleeve surrounding the distal longitudinal end portion of the flange portion has a rounded exterior periphery having a substantially uniform radial extent from the rounded exterior periphery of the free longitudinal end portion of the flange portion.

The rounded exterior periphery of the second longitudinal end portion of the skin contact pad may be substantially semi-circular, and wherein the rounded exterior periphery of the distal longitudinal end portion of the flange portion and the rounded exterior periphery of the free longitudinal end portion of the integral sealing sleeve are concentric with the rounded exterior periphery of the second longitudinal end portion of the skin contact pad.

The the skin contact pad may have an oval sports field shape.

The electrode main body is elongate and may have a substantially uniform thickness, and wherein the signal transmission pad has a resistance which is more than three times the resistance of the signal collection portion.

The flexible, conductive and resilient material may be selected from a group consisting of carbonized elastomer, nickel or copper plated polyester, silver nylon mesh, cotton silver bamboo fiber, and conductive fabrics selected from a group consisting of metalized fabrics and carbonized fabrics.

An ECG signal collection strap for collecting ECG signals has been disclosed. The ECG signal collection strap comprises a first ECG signal collection electrode and a second ECG signal collection electrode which are mounted on an elongate stretchable textile strap, wherein each of the ECG signal collection electrodes comprises a signal collection portion comprising a signal collection pad, a signal output portion comprising a signal output pad, and a signal transmission portion interconnecting the signal collection portion and the signal output portion and comprising a signal transmission pad.

The textile strap may have a width comparable to or slightly larger than to the width of the signal collection portion of the electrode.

The signal transmission portion may have a resistance which is more than three times the resistance of the signal collection portion.

BRIEF DESCRIPTION OF FIGURES

The disclosure is described with reference to the accompanying Figures, in which:

FIG. 7B1 is a front elevation view of the example electrode of FIG. 7, and FIGS. 8A and 8B are plan and perspective views showing an inward facing side of an example ECG electrode.

DETAILED DESCRIPTION OF EXEMPLARY EMBODIMENTS

The strap of FIGS. 1 to 5A is a chest-worn ECG signal collection strap apparatus (more commonly known to as a 'chest strap') illustrating an exemplary embodiment of a physiological signal collection strap of the present invention. The chest strap 100 comprises first 120 and second 140 ECG signal collection electrodes which are mounted on an elastic strap 180. The elastic strap is made of a breathable and insulating material, such as a fabric comprising a mixture of polyamide and an elastomer. Each of the signal collection electrodes 120, 140 comprises a signal collection pad and a signal output portion. Each signal collection pad comprises a flexible signal collection surface which is arranged to contact the skin and collect ECG signals from a user during use.

Figure 1:
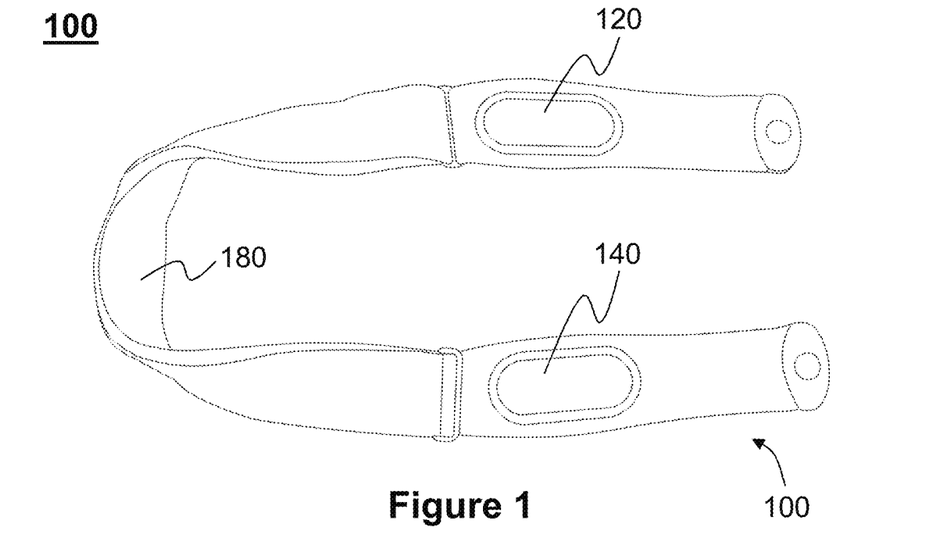
FIG. 1 is a perspective view of an example chest strap illustrating a first embodiment of the present invention, FIGS. 2 and 3 respectively show the front and rear views of the chest strap of FIG. 1.
Figure 2:
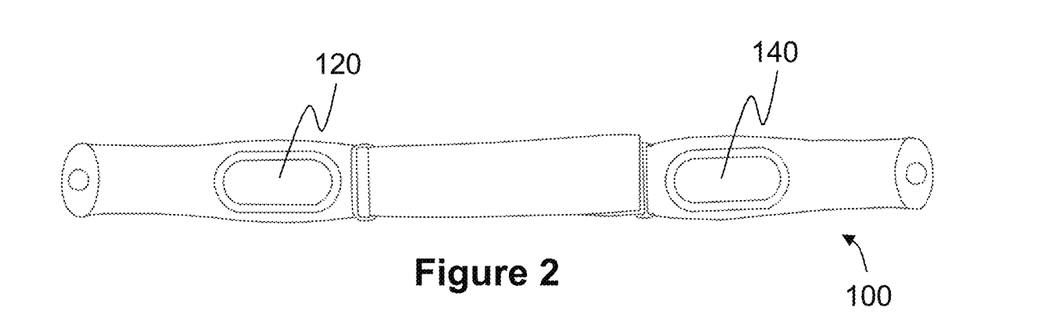
Figure 3:
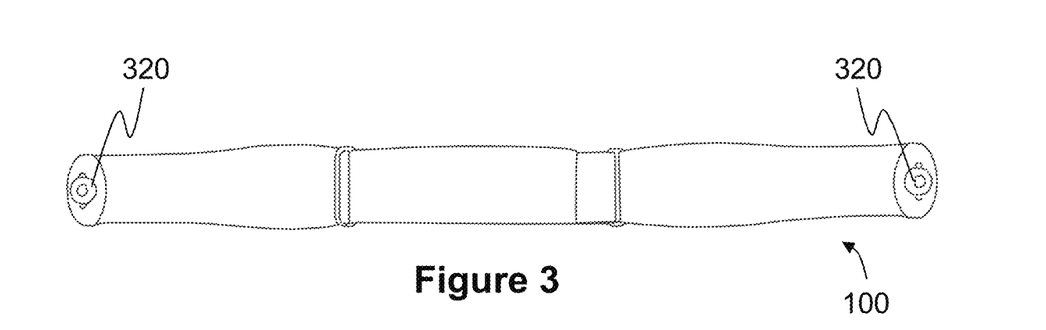

A carbonized rubber pad as an example of a flexible signal collection pad is used to collect ECG signals from the chest of a user. The flexible signal collection pad is arranged such that it is urged and pressed against the skin of a user by the tension, more particularly the body-bound tension, of the elastic strap during use when the elastic strap is tightened on the body of the user to minimize contact resistance between the skin and the signal collection pad. The flexible collection surface are arranged to transmit collected ECG signals to a signal output portion which is terminated at a conductive fastening component located at a longitudinal end of the strap. The conductive fastening components of the two ECG signal collection electrodes are located at opposite longitudinal ends of the strap and are arranged to convert the longitudinal strap into a strap loop when the fastening components are respectively anchored onto corresponding or counterpart fastening components. Each conductive fastening component comprises a mechanical mating portion which is adapted for making counterpart engagement with another compatible mechanical mating portion of a compatible fastener. Example of suitable fasteners includes a snap fit fastener or a magnetic clasp.

Each of the signal collection electrodes is mounted on the insulating fabric strap with the signal output portion located at or proximal to a free longitudinal end of the strap such that the two signal output portions are located at the two extreme or free longitudinal ends before the chest strap is converted into a chest strap loop. In this condition, the two signal collection pads are located intermediate the two conductive fasteners which are located at the free longitudinal ends of the strap. To provide good mechanical fastening and good electrical contact, the signal output portion of the signal collection electrode is riveted onto the chest strap by a rigid conductive fastener, which conductive fastener also operates as a signal output terminal to deliver ECG signals from the chest strap for further processing.

In order that ECG signals can be effectively collected from the chest of a user, the signal collection pads of the two ECG signal collection electrodes are disposed on the strap such that when the fastening components are mechanically connected with the respective counterpart or corresponding fastening means to form a tensioned strap loop and duly worn and aligned on the chest of a user, the signal collection surfaces will be attached respectively to the left and right portions of the rib cage of the user. To adapt for this application, the distance between the two signal collection surfaces is equal to or approximately equal to the distance between the portions of the rib cage left and right of the sternum when the chest strap loop is duly worn. In order to provide adequate separation between the two signal collection surfaces during use, the signal collection pad of a signal collection electrode is connected to its corresponding signal output portion via a bridging portion which is adapted to provide spatial separation between the signal collection surface and the signal output portion. For good signal continuity, the signal collection pad, the bridging portion and the output portion are integrally molded of carbonized rubber as an example of a flexible and conductive substance. It will be noted that the molded flexible electrode is substantially planar for wearing comfort. The chest strap also comprises a strap length adjustment mechanism for adjusting the effective or usable length of the chest strap to cater for users of different chest widths.

Construction of an exemplary chest strap will be described in more detail below. The elastic strap comprises first and second elongate fabric layer strips which are glued together to form a double-layered strap. Each of the fabric layers are made of an insulating and elastic fabric, such as a mixture of polyamide and elastomer. A breathable fabric which is moisture permeable is preferred for comfort wearing. The planar electrode is sandwiched or embedded between the two fabric layers, while leaving the signal collection surface and the signal output portion exposed for external electrical contact. The regions of the unexposed planar electrode are also glued to the elastic strap for durability. A bonding agent is applied to the periphery of the exposed signal collection surface to further bond the signal collection pad to the strap and to provide a smooth edge. As an optional feature, the back surface of the elastic strap, which is the surface adapted to be in contact with the skin of a user, is formed with a woven anti-slid texture. As a further option, the material composition of the two strap layers could be different. For example, the textured layer may be made of 37% elastomer while the non-textured layer comprises less than 20% elastomer.

Figure 4:
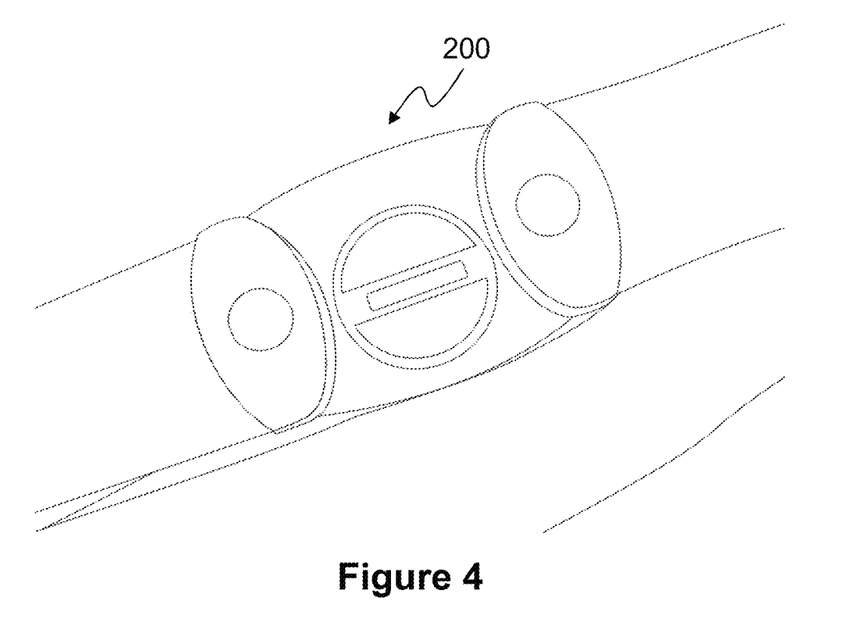
FIG. 4 shows the strap of FIGS. 1-3 when fastened with an ECG processing apparatus.
Figure 4A:
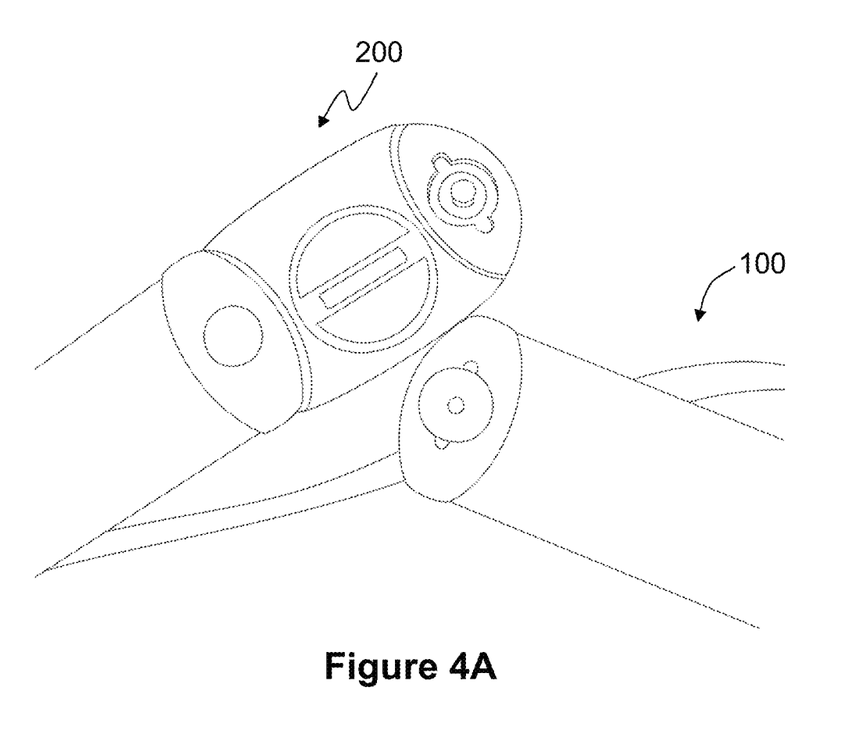
FIG. 4A shows the strap of FIG. 4 when the ECG processing apparatus partly detached from the chest strap.
Figure 5:
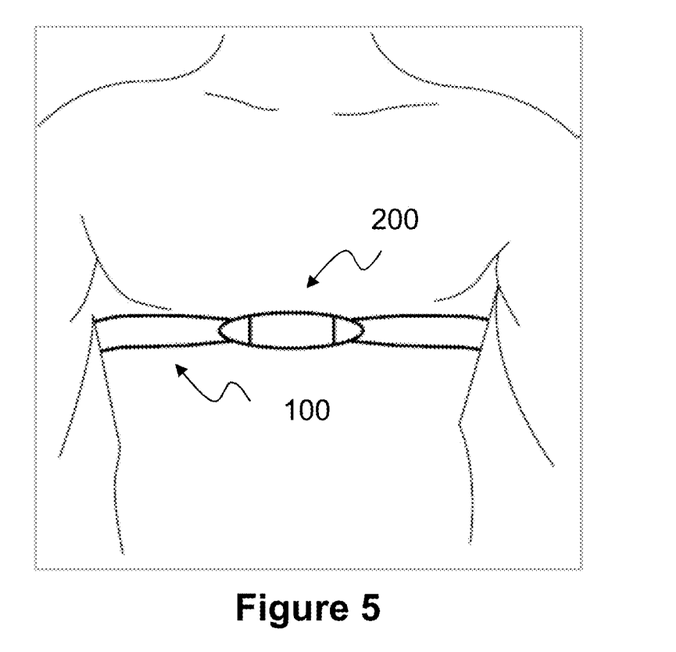
FIG. 5 is a schematic view illustrating the chest strap of FIG. 1 in use.
Figure 5A:
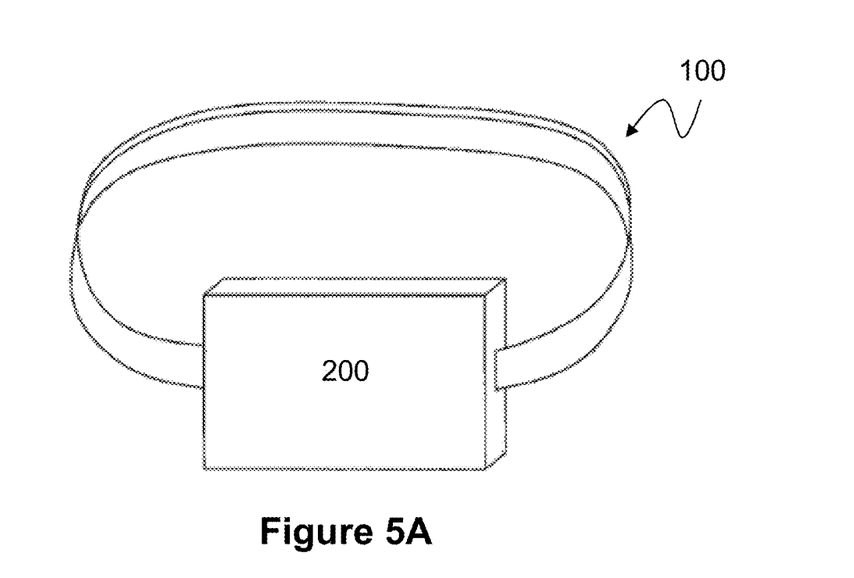
FIG. 5A is an enlarged view showing the chest strap of FIG. 1 in combination with an ECG signal processor.

In an exemplary use of the chest strap as shown in FIGS. 4, 4A & 5, the chest strap is illustrated when used in combination with a mobile ECG signal processor 200. The ECG signal processor includes a rigid housing and a pair of signal input terminals. Each signal input terminal is a fastening component having a rigid mechanical mating portion which is configured to engage with a corresponding fastening component of the chest strap. The distance between the two signal collection surfaces in this application configuration therefore includes the longitudinal separation between the two fastening components on the mobile ECG signal processor. The ECG signal processor includes means for capturing and processing the detected ECG signals, as well as optional features for transmitting the relevant data to an external device for further processing or storage.

Figure 6:
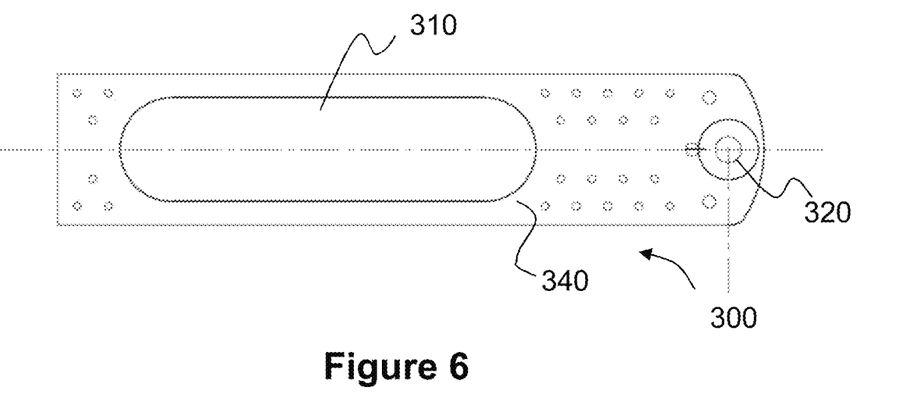
FIG. 6 is a plan view of a first embodiment of an ECG electrode covered with an insulator.
Figure 6A:
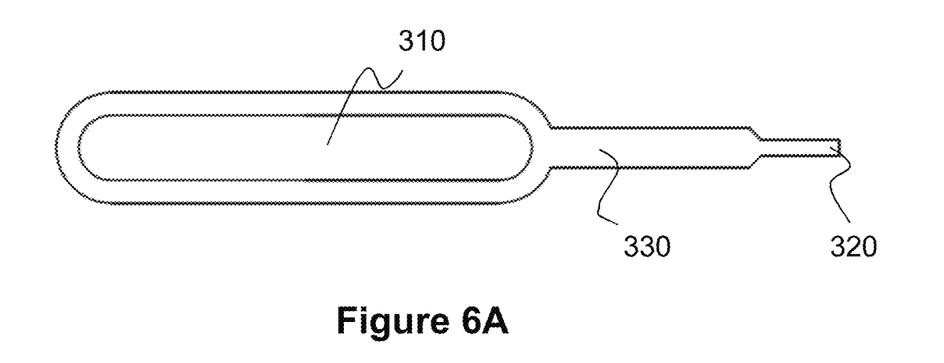
FIGS. 6A and 6B are respectively plan and side views of the electrode alone.
Figure 6B:
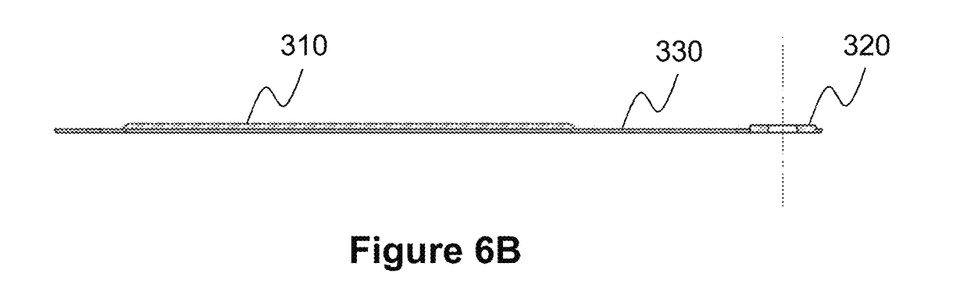
Figure 6C:
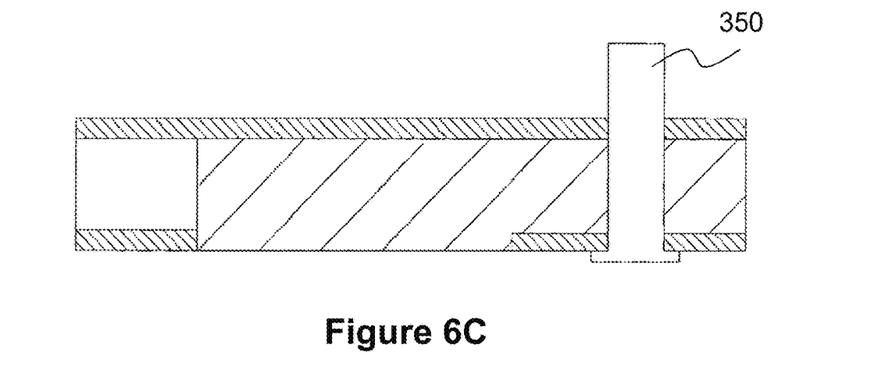
FIG. 6C is a schematic side view illustrating the electrode of FIG. 6 connected with an output terminal.

Referring to FIGS. 6 to 6C, there is shown an embodiment of a signal collection electrode 300 comprising a flexible contact pad 310, a signal output portion 320 and a bridging portion 330 interconnecting the flexible contact pad and the signal output portion. The signal collection electrode is integrally molded of carbonized rubber and is substantially planar and elongate. As is better seen in FIGS. 6B and 6C, the flexible contact portion 310 protrudes above the bridging portion to form an elevated signal collection surface. The entire electrode, except for the signal collection surface and the signal output portion, is covered by an insulator, which is for example a molded rubber sleeve 340. The rubber sleeve 340 comprises optionally perforations to improve permeability. A mechanical fastening component, for example a snap fastener part, is formed through the signal output portion to form the signal output terminal 350.

Figure 7:
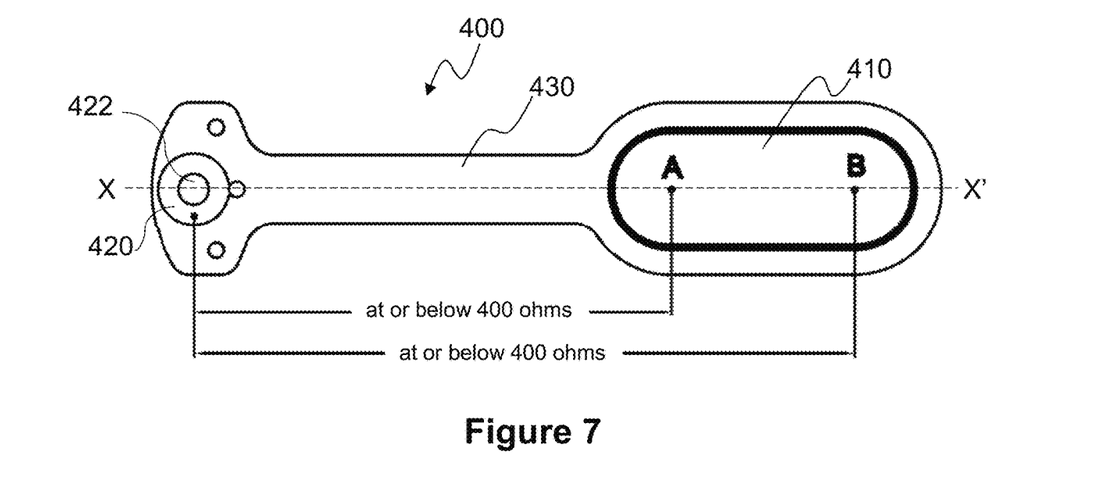
FIG. 7 is a plan view showing an inward facing side of an example ECG electrode.
Figure 7A:
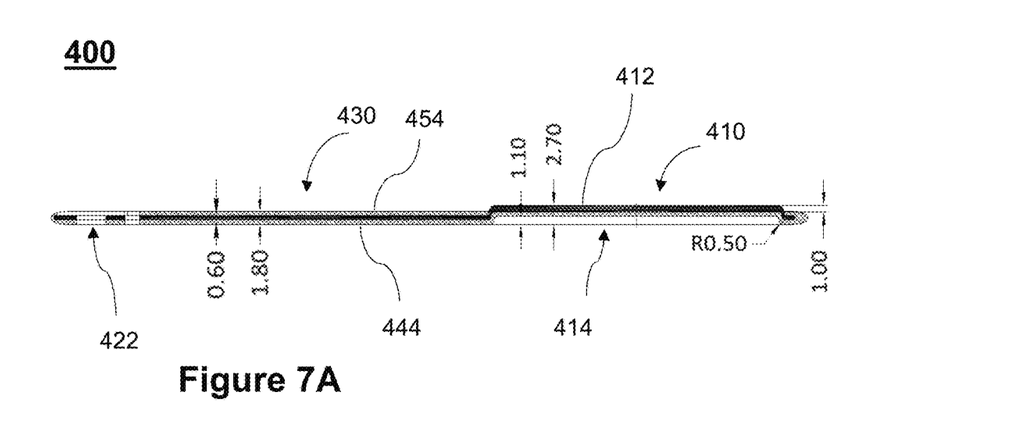
FIG. 7A is a longitudinal cross-sectional view of the example electrode of FIG. 7 taken along the longitudinal axis X-X'.

The electrode 400 of FIGS. 7 & 7A also comprises a flexible contact pad 410, a signal output portion 420 and a bridging portion 430 and is integrally molded of a flexible and resilient conductive substance. The bridging portions of the electrodes of FIGS. 6 & 7 are narrower than the width of the signal collection surface. Such a narrowed bridging portion of a resilient material provides additional elasticity to strength the chest strap. In addition, the narrowed bridging portion also eliminates the need of extra breathing perforations.

As an alternative, the bridging portions of the electrodes could be of a same or comparable width to that of the signal collection surface, and perforations may be optionally formed outside the signal collection surfaces to improve breathability.

Regardless of the specific electrode designs, each of the signal collection pad is configured so that the effective area of the distributed signal collection surface could collect reasonable ECG signals for meaningful processing. The effective area here refers to the surface which exposes through the fabric strap and which has a typical width of about 1.5 to 2.5 cm and a typical length of about 5-8 cm. The resistance of the electrode, measured between the signal collection pad and the signal output portion, is typically below 1 kΩ, for good signal processing and operation.

In an exemplary use of the chest strap for swim applications, the electrode resistance is typically below 1,000Ω, preferably below 700Ω, and more preferably below 500Ω, and even 400Ω. It is noted that such a low resistance provides a useful solution to enable ECG signal collection in both sea and chlorinated water. When using as a swim chest strap, the bridging portion is insulated by a molded collar which is mold over the electrode, leaving only the signal collection surface and the signal output portion exposed. The insulated bridging portion mitigates signal leakage or interference when the chest is used in a highly conductive medium such as sea or chlorinated water.

A physiological signal collection electrode disclosed herein comprises a signal collection portion, a signal transmission portion and a signal output portion. The signal collection portion, the signal transmission portion and the signal output portion are integrally formed into a single body.

The signal collection portion comprises a flexible conductive pad comprising a substantially planar and flexible conductive member. The signal collection electrode is for wearing on the body of a user and the inward facing side is to face the body of a user during use when physiological signals such as ECG signals are being collected by the signal collection electrode. The inward facing side is also referred to as a body facing side. The signal collection portion comprises a skin contact pad 416 on one side of which is defined skin contact surface. The skin contact surface is for making physical and electrical contact with the skin of a user to facilitate collection of physiological signals from the skin of a user. The skin contact pad is part of a signal collection pad and the skin contact surface is a signal collection surface. The signal collection surface is on the body facing side of the signal collection pad. The skin contact pad comprises an outward facing surface which is on an outward facing side of the skin contact pad. The outward facing side is on another side of the skin contact pad which is an opposite facing side to the inward facing side.

The signal output portion is for outputting physiological signals collected by the signal collection portion, for example, to an external processing apparatus and comprises a signal output pad on which a signal output surface 424 is defined. The signal output surface is to facilitate making of physical and electrical contact with an input terminal of a signal receiver of the external processing apparatus and comprises an output contact portion. The signal output portion comprises a flexible conductive pad comprising a substantially planar and flexible conductive member. In some embodiments, a built-in signal output terminal is formed on the signal output portion to facilitate output of collected signals. The signal output terminal may be integrally formed on the output contact portion or may be attached to the output contact portion by fastening, for example, by riveting, by fusion joining, or by gluing using a conductive glue. In the embodiment of FIG. 7, a signal output terminal is formed integrally as a signal outputting ring having an internal aperture 422. In some embodiments, the signal output terminal is formed integrally on the signal output portion as a conductive protrusion.

The signal transmission portion interconnects the signal collection portion and the signal output portion. The signal transmission portion defines a conductive bridging portion which interconnects the signal collection portion and the signal output portion to facilitate transmission or transfer of collected signals from the signal collection portion to the signal output portion. The signal transmission portion comprises a flexible conductive pad comprising a substantially planar and flexible conductive member When used as ECG electrodes of an example chest strap, a first electrode is attached to the left rib-cage of a user, a second electrode is attached to the right rib-cage of a user, and the signal transmission portions of the first and second electrodes extend from their respective signal collection portions towards each other so that the output contact portions of the electrodes are at a separation distance to connect with the input terminals of a signal receiver.

The signal collection pad, the signal transmission pad and the signal output pad collectively define a main electrode body of the signal collection electrode. The main electrode body is substantially a flexible and conductive flap which comprises a substantially planar and flexible conductive member having an inward facing side which is a side that faces the skin of a user during use and an outward facing side which is opposite facing to the inward facing side.

Referring to FIGS. 7, 7A, 7B and 7B1, the main electrode body of the signal collection electrode comprises an elongate band-like conductive body which extends along a longitudinal axis X-X' and has a substantially uniform thickness between the inward facing surface and the outward facing surface along its length.

The signal transmission portion extends along a longitudinal axis between the signal collection portion and the signal output portion. The signal transmission portion is elongate and substantially rectangular, extends along and symmetrical about the longitudinal axis X-X', is band-like, and has a substantially uniform thickness between the inward facing surface and the outward facing surface along its length.

The signal transmission portion comprises a conductive signal transmission pad which is an elongate band-like conductive member having a thickness which is substantially smaller than its length (along the longitudinal direction of the longitudinal axis) and its width (in a direction transversal to the longitudinal direction). The signal transmission pad has an inward facing surface and an outward facing surface, and its thickness is the separation distance between the inward facing surface and the outward facing surface. The signal transmission pad is optionally made of a conductive elastomer such as a carbonized elastomer.

The signal transmission pad is sealed by a waterproof sealing means to mitigate and minimize signal leakage during under water use, for example, when the electrode is worn by use during swimming and the electrode is totally immersed in water, for example, sea water or chlorinated water. In this example, the signal transmission pad is sealed by an electrically insulating and waterproof sleeve which is over-molded or laminated onto the conductive member. The sleeve may be made of a flexible, resilient, non-conductive and waterproof elastomeric material, such as rubber, plastics or silicone rubber. When the sleeve is laminated or over-molded onto the conductive member of the signal transmission portion, for example, by thermal over-molding, signal transmission pad is tightly sandwiched between two layers of flexible, resilient, non-conductive and waterproof material, and is physically and electrically insulated from the surrounding water in which the electrode is immersed during under water use.

The signal collection portion comprises a signal collection pad and an insulating sleeve to waterproof the signal collection pad. The signal collection pad comprises a skin contact pad and a flange portion 415. The skin contact pad has a skin contact surface on its inward facing side and a peripheral wall 413 surrounding the skin contact surface. The skin contact surface is parallel to the longitudinal axis and the peripheral wall extends between an inward end and an outward end to displace the skin contact surface axially inwardly with respect to the signal transmission pad. The terms axially and axial direction herein means a direction along which the skin contact surface is to enter into abutment contact with the skin of a user. The flange portion 415 extends radially away from the outward end of the peripheral wall 413 and surrounds the peripheral wall. The outward end is the end which is distal to the skin contact surface. The flange portion 415 extends around the signal collection pad except where the signal collection portion joins the signal transmission pad. The peripheral wall 413 also extends at its outward end to join the signal transmission pad. The flange portion projects radially away from the outward end of the peripheral wall 413 and has a substantially uniform radial extent on extending around the signal collection pad. The example flange portion is at the same axial level as the signal transmission pad and is on the longitudinal axis. The radial extent of the flange portion is comparable to the thickness of the skin contact pad or slightly larger.

The signal collection pad has an inward facing surface on which the signal collection surface 412 is defined and an outward facing surface which is on the outward facing side and facing away from the body of a user. The signal collection pad is a substantially band-like member having a thickness which is substantially smaller than its length and its width. The signal collection pad is elongate, extends along the longitudinal axis X-X', is band-like, and has a substantially uniform thickness between the inward facing surface and the outward facing surface along its length. The signal collection portion is optionally symmetrical about an axis of lateral symmetry and the signal transmission portion is also optionally symmetrical about the same axis of lateral symmetry, which is the longitudinal axis in this example.

Figure 7B:
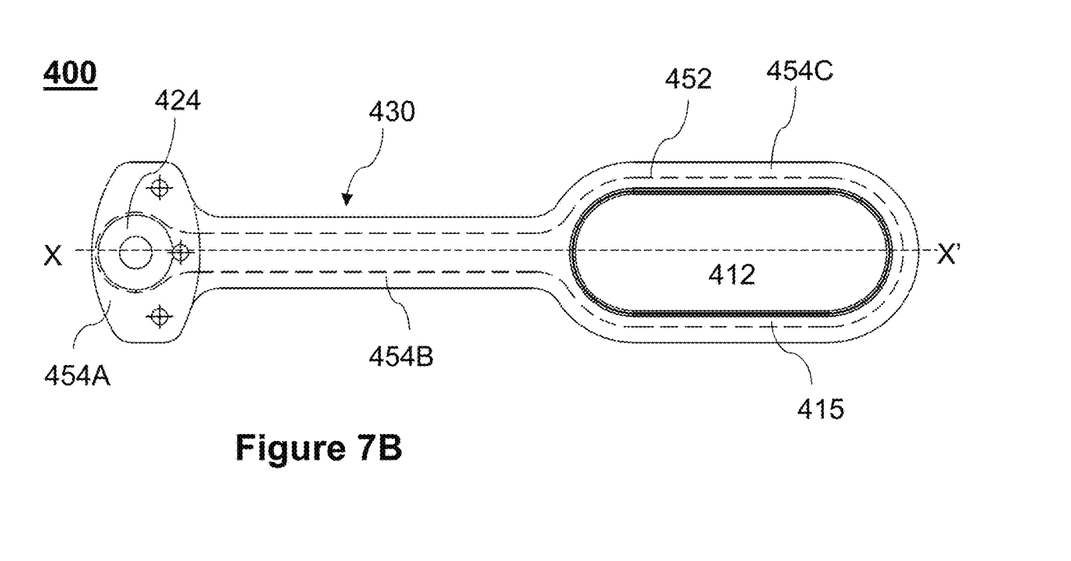
FIG. 7B is a plan view showing an inward facing side of the example ECG electrode of FIG. 7 and internal details.
Figure 7B:
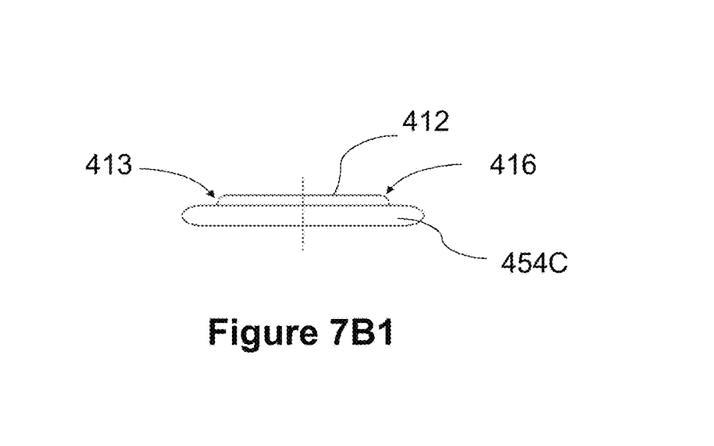

The skin contact surface 412 is inwardly displaced with respect to the signal transmission portion, as depicted in FIGS. 7A and 7B1. More specifically, the skin contact surface 412 is inwardly displaced with respect to the signal transmission pad by the peripheral wall along an axial direction, the axial direction being a direction along which the skin contact surface is to enter into abutment contact with the skin of a user. The extent of inward displacement of the skin contact surface is equal to the height of the peripheral wall, and the height of the peripheral wall is measured in the axial direction. In this example, the skin contact pad and the signal transmission pad have approximately the same uniform thickness and the skin contact surface is parallelly displaced inwardly from the signal transmission pad by a height defined by the peripheral wall. The skin contact pad protrudes inwardly with respect to the signal transmission pad and with respect to the insulating sleeve 454C which surrounds the peripheral wall and which forms a waterproof lamination around the flange portion, as depicted in FIGS. 7A and 7B1. The protruding portion of the signal collection pad forms a raised platform, a raised signal collection surface, and a shallow cavity or a shallow compartment. The flange portion provides a peripheral surface around the signal collection surface to facilitate more reliable attachment to a substrate, for example, a strap of textile.

The signal collection pad, except the signal collection surface and optionally a portion of the peripheral wall, is sealed by a waterproof sealing means to mitigate and minimize collection of spurious, unwanted or interference signals during under water use. For example, the signal collection pad may be sealed by over-molding or laminating a water impervious and electrically insulating sleeve portion 454C around the radially extending flange portion and onto the outward facing surface of the skin contact pad. The sleeve portion 454C may be made of a flexible, resilient, non-conductive and waterproof material, such as rubber, plastics or silicone rubber. When the sleeve is laminated or over-molded onto the signal collection pad, the flange portion and the outward facing surface of the signal collection portion is imperviously covered by a layer flexible, resilient, non-conductive and waterproof material, and is electrically insulated from the surrounding water during under water use. In this example, the sleeve portion of the signal collection portion and the sleeve portion of the signal collection portion are integrally formed. As shown in FIGS. 7B and 7B1, the flange portion is peripherally sealed by a watertight lamination formed by the integral sealing sleeve and the skin contact pad protrudes inwardly with respect to the sealing sleeve. The integral sealing sleeve wraps round the flange portion and covers the outward facing surface of the skin contact pad to form a waterproof lamination on the signal collection portion.

The signal output pad except at the signal output surface is sealed and insulated by a waterproof sealing means to mitigate and minimize leakage of collected signals during under water use. For example, the signal output pad may be sealed by over-molding or laminating a water impervious and electrically insulating sleeve onto the signal output portion except at the output contact portion. In this example, the sleeve portion 454C of the signal collection portion, the sleeve portion of the signal transmission portion 454B and the sleeve portion 454A of the signal output portion are integrally formed into a single piece of watertight or water impervious electrode sleeve 454 to enclose or to embed the main electrode body of the electrode in a watertight environment except at the signal collection surface 412 and the signal output surface 424. The main electrode body of the signal collection electrode has an exterior boundary 452 which is indicated by a dotted line on FIG. 7B, and the exterior boundary of the signal collection electrode is defined by the sleeve 454. The dotted line also shows the exterior boundary of the flange portion.

The signal collection surface extends between a first longitudinal end which is proximal to the signal transmission portion and a second longitudinal end which is distal to the signal transmission portion. The signal collection surface includes a first longitudinal end portion comprising the first longitudinal end, a second longitudinal end portion comprising the second longitudinal end, and an intermediate portion interconnecting the first longitudinal end portion and the second longitudinal end portion. The intermediate portion of the signal collection pad is substantially rectangular and has a substantially uniform width in this example. The width of the intermediate portion is substantially larger than the width of the signal transmission portion. In this example, the ratio is slightly larger than three. Each of the first longitudinal end portion and the second longitudinal end portion is a semi-circular portion having a semi-circular outline profile. The semi-circular outline profile of the first longitudinal end portion is a convexly curved portion opposite facing the signal transmission portion and the semi-circular outline profile of the second longitudinal end portion is a concavely curved portion opposite facing the signal transmission portion. The first longitudinal end portion continues from the intermediate portion and tapers to narrow as it extends towards the signal transmission pad. The peripheral wall proximal the first longitudinal end converges to connect the first longitudinal end of the signal collection surface to the signal transmission pad.

A longitudinal end of the first longitudinal end portion which is proximal the intermediate portion is flush with the intermediate portion and joins or merges with the intermediate portion smoothly. In this example, the first longitudinal end portion follows the curvature of a semi-circle as it flares to widen to join the intermediate portion, and the semi-circle has a diameter which is the same as the width of the intermediate portion. Each of the first longitudinal end portion and the second longitudinal end portion curves to widen to join the intermediate portion with a smooth transition.

The flange portion has a substantially uniform radial extent from the peripheral wall and follows the rounded profile of the first longitudinal end portion at its longitudinal free end. As depicted in FIG. 7A, the flange portion and the signal transmission pad are at approximately the same axial level and has approximately the same thickness.

In the example electrode of FIG. 7, the signal collection surface has an overall shape of an oval sports field, the main electrode body has a thickness of about 0.6 mm, the signal transmission portion including the sleeve has a thickness of about 1.8 mm and a width of about 11 mm, the signal collection surface has an area of slightly smaller than 10 cm square, the electrode has a length of about 128 mm, the signal collection surface has a length of about 50 mm and a width of about 20 mm at its intermediate portion, and the signal transmission pad has a width of about 6 mm. The ratio of the width of the signal transmission pad to the width of the intermediate portion is optionally between 1 and 0.25, and preferably between 0.6 and 0.25. For example, the ratio may be at or less than 0.6, at or more or less than 0.5, at or more or less than 0.4, at or more or less than 0.3, at or more than 0.25, or any range or ranges selected from the aforesaid values or limits. The example electrode is compact and has an overall dimension of about 13 cm×2.8 cm, a longitudinal separation distance of about 9.2 cm between the longitudinal centers of the signal collection surface and the signal output surface, a longitudinal separation distance of about 6.3 cm between the first longitudinal end of the skin contact pad and the center of the signal output surface. It has been found that a skin contact surface having a length of about 5.5 cm to 6.5 cm and a width of about 18 cm to 25 cm and a longitudinal separation distance of about 8.8 cm to 9.5 cm between the longitudinal centers of the signal collection surface and the signal output surface provide an optimal coverage for most of the population when used as an ECG electrode on a ECG chest strap such as the chest strap of FIG. 1 on which a pair of electrodes is mounted.

As the signal transmission pad has a smaller width than the signal collection surface, collected signals will be concentrated into the signal transmission portion when transiting from the signal collection surface 412 to the signal output surface 424. On the other hand, a signal transmission pad which is narrower than the signal collection surface means that the signal transmission pad has a higher per-unit-length resistance. With a width ratio of the signal transmission pad to the intermediate portion between 0.6 and 0.25, the resistance-per-unit-length ratio is approximately between 1.66 and 4.

For example, where the width of the signal transmission pad is about one-third of the width of the signal collection surface as in the present example, the per-unit-length resistance of the signal transmission pad is about three times the per-unit-length resistance of the signal collection surface, given that the signal transmission pad and the signal collection pad have the same thickness. In this example, the total signal resistance of the electrode is at 400 ohm or slightly less than 400 ohm, the signal path resistance of the signal transmission portion is slightly less than 300 ohm and the signal path resistance of the signal collection pad is slightly less than 100 ohm.

While a wider signal transmission pad will have a lower per-unit-length resistance, it has been found that a narrower signal transmission pad in combination with a wider signal collection pad coupled with the integral sealing means would result in enhanced waterproof performance. Furthermore, it has been found that a wider pad of carbonized rubber when subject to thermal treatment, for example, thermal lamination or thermal over-molding, will result in somewhat unpredictable increases in resistance and is therefore not preferred. A width ratio of the signal transmission pad to the intermediate portion between 0.6 and 0.25 has been found to achieve a good balance between good signal reception, good production yield and good waterproof performance. A pair of electrodes each having a signal path resistance of less than 500 ohm or 400 ohm coupled with the width ratio of 0.6 and 0.25 when attached to a stretchable textile chest strap to operate as an underwater heart rate chest strap was been found to perform well even in sea water and chlorinated water (swimming pools) applications.

The signal output portion has a width which is comparable to the width of the intermediate portion of the signal collection surface. The enlarged width of the signal output portion facilitates reliable output signal connection and the signal output portion has the appearance of a fish-tail.

Figure 8A:
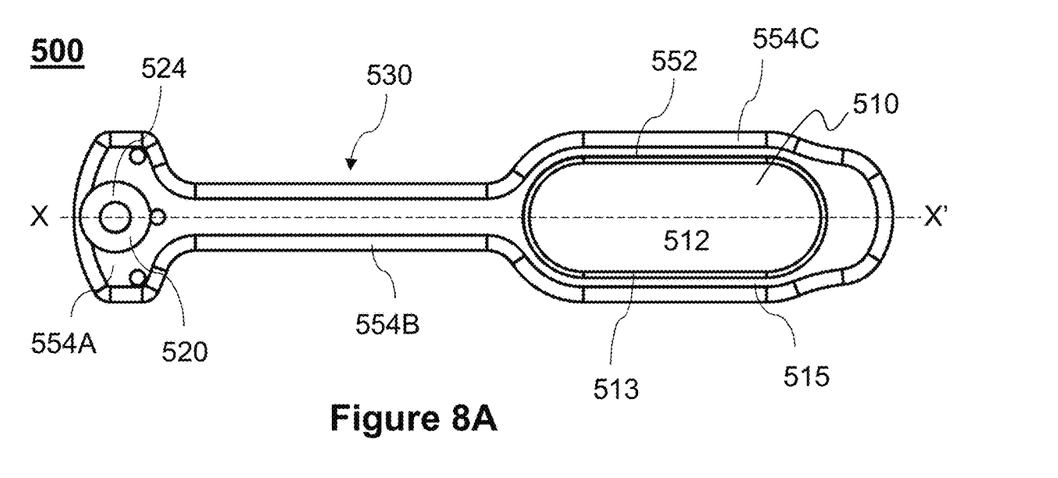
Figure 8B:
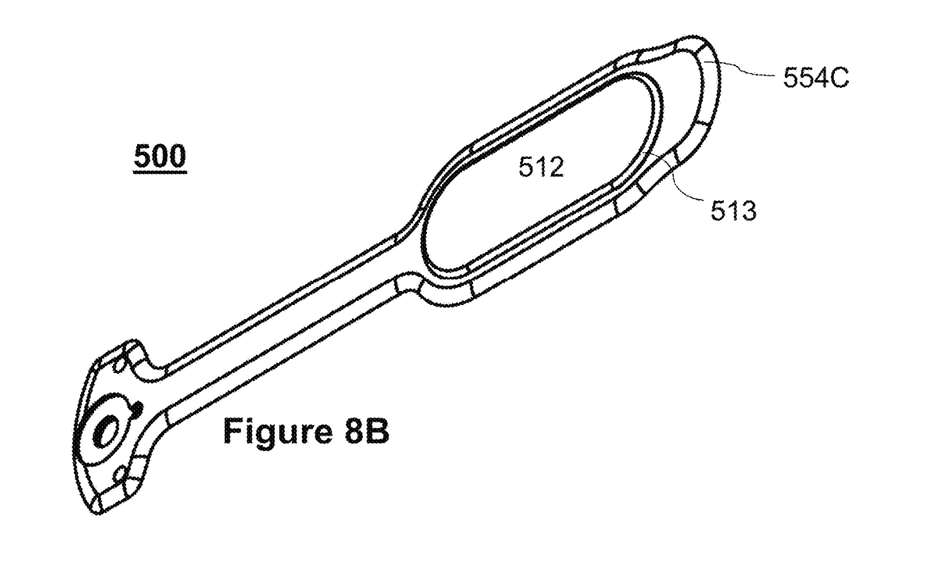

An example electrode 500 depicted in FIGS. 8A and 8B comprises a signal collection portion 510, a signal transmission portion 530 and a signal output portion 520. The electrode 500 is substantially identical to the electrode 400 except that the portion of the insulating sleeve along the lateral periphery of the main electrode body has a higher thickness than the portion outside the lateral periphery, and the flange portion at the longitudinal free end of the skin contact pad is longer. The description on and in relation to the electrode 400 is incorporated herein for succinctness and to apply to the electrode 500 mutatis mutandis with corresponding numerals increased by 100.

To form an ECG chest strap, for example, an ECG chest strap of FIG. 1, using the ECG electrodes described herein, a first ECG electrode and a second ECG electrode are mounted on the elastic textile strap, for example, by using a thermal bonding agent. For example, a pair of ECG electrodes wherein each electrode is an electrode 400 or 500 is mounted on the strap 180 in longitudinal alignment. The ECG electrodes are mounted such that the signal output portions are proximal to each other and the signal collection portions are distal to each other. Where the strap has two longitudinal free ends, the signal output portions are mounted at or near the free ends. To facilitate detachable mechanical and electrical connections between the electrodes and a signal receiver having input connectors, a signal output terminal is attached to a signal output surface of the electrode. The signal output terminal may be a male connector or a female mechanical and electrical connector and may be fastened to the strap by riveting or other fastening means. To make the signal output portion more robust and durable, a terminal guard, for example, a terminal guard made of hard plastics is formed on the signal output portion and surround the signal output terminal. To facilitate collection of ECG signals, a signal collection aperture which is matched with the protruding signal collection surface of the electrode is formed on each side of the strap and the electrodes are mounted with their signal collection surface exposing through the signal collection apertures. The electrodes may be mounted on the chest strap by applying a thermal bonding glue on the inward facing side of the insulating sleeve, placing the electrodes on the strap such that the inward facing side is in abutment with a bonding surface of the strap and then apply heat and pressure to form adhesive bonding between the strap and the electrodes. In some embodiments, the textile strap comprises two layers, the electrodes may be mounted on the chest strap by applying a thermal bonding glue on both the inward facing side and the outward facing side of the insulating sleeve, placing the electrodes on the strap between the two layers such that the inward facing side is in abutment with a first inner bonding surface on a first layer of the strap and the outward facing side is in abutment with a second inner bonding surface on a second layer of the strap, and then apply heat and pressure to form adhesive bonding between the strap and the electrodes. It is noted that thermal bonding of the electrodes onto the strap results in somewhat unpredictable or erratic increases in resistance of the electrode, especially when the width is wide. It is therefore desirable to reduce the width of the main electrode body. On the other hand, reducing width means increasing resistance and is adverse for underwater ECG signal detection and is undesirable. The electrodes disclosed herein are a result of balance between various design factors to facilitate underwater ECG signal detection, especially under water ECG detection using a textile chest strap, and represents an advance in the art.

While the present disclosure has been explained with reference to the embodiments above, it should be appreciated that the embodiments are only described to illustrate the invention and are not meant for restricting the scope of invention. For example, while a swim monitor strap has been illustrated as an example, a strap of the present invention could be used for running or other activities without loss of generality.

| Table of Numerals | | |
|---|---|---|
| 100 | | Chest strap |
| | 120 | First ECG signal collection electrode |
| | 140 | Second ECG signal collection electrode |
| | 180 | Strap |
| 200 | | Mobile ECG signal processor |
| 300 | | Signal collection electrode |
| | 310 | Contact pad |
| | 320 | Signal output portion |
| | 330 | Bridging portion |
| | 340 | Sleeve |
| | 350 | Signal output terminal |
| 400 | | Electrode |
| | 410 | Contact pad |
| | 420 | Output portion |
| | 430 | Bridging portion |

The invention claimed is:

1. An ECG electrode for collecting ECG signals in sea or chlorinated water, comprising an elongate and conductive elastomeric electrode body on which a first portion, a second portion, and a third portion interconnecting the first portion and the second portion are defined;
wherein the first portion comprises a signal collection portion including a signal collection pad, the second portion comprises a signal output portion including a signal output pad, and the third portion comprises a signal transmission portion including a signal transmission pad for transmitting ECG signals collected by the signal collection portion to the signal output portion;
wherein a signal output terminal for outputting collected ECG signals is disposed on the signal output portion;
wherein the signal collection portion defines a signal collection surface and peripheral portion surrounding the signal collection surface, the signal collection surface protruding above the peripheral portion;
wherein an insulating and elastomeric sealing sleeve is integrally moulded on the conductive elastomeric electrode body to cover the first portion, the second portion and the third portion, leaving the signal collection surface and the signal output terminal un-covered;
wherein the conductive elastomeric electrode body has a resistance of 400 ohm or less, the resistance being measured between the signal collection surface and the signal output terminal; wherein a width ratio of the signal transmission pad to the signal collection surface is between 0.6 to 0.25; and the ECG electrode is provided on a chest strap adapted to be worn by a user; wherein the ECG electrode is adapted to acquire ECG signals when the chest strap is worn by the user and immersed in sea or chlorinated water.

2. The ECG electrode of claim 1, wherein the signal collection pad, the signal transmission pad and the signal output pad are disposed sequentially along a longitudinal direction defined by a longitudinal axis.

3. The ECG electrode of claim 2, wherein the signal collection pad has a tapered longitudinal end portion which joins the signal transmission pad, and wherein the insulating and elastomeric sealing sleeve has a tapered profile which follows the tapered longitudinal end portion of the signal collection pad.

4. The ECG electrode of claim 3, wherein the tapered longitudinal end portion of the signal collection pad is a rounded end which tapers gradually and smoothly to merge with the signal transmission pad.

5. The ECG electrode of claim 4, wherein the signal output pad has a tapered end portion which joins the signal transmission pad, and wherein the insulating and elastomeric sealing sleeve has a tapered profile which follows the tapered end portion of the signal output pad.

6. The ECG electrode of claim 2, wherein the insulating and elastomeric sealing sleeve comprises an end portion which surrounds the signal output terminal.

7. The ECG electrode of claim 1, wherein the signal output terminal is configured as a mating portion of a conductive mechanical fastener.

8. The ECG electrode of claim 1, wherein the third portion is a narrowed bridging portion which interconnects the first portion and the second portion, wherein the first portion has a tapered portion which tapers to join the third portion, and wherein the insulating and elastomeric sealing sleeve has a tapered profile which follows the tapered portion of the first portion.

9. The ECG electrode of claim 1, wherein the signal output terminal is configured as a mating portion of a metallic snap fastener.

10. The ECG electrode of claim 1, wherein the peripheral portion comprises a peripheral flange, and wherein the insulating and elastomeric sealing sleeve is over-molded on the peripheral flange to surround the signal collection surface.

11. The ECG electrode of claim 10, wherein the peripheral flange has a first end portion which is in abutment with the signal transmission pad and which comprises a first rounded corner and a second rounded corner, wherein each of the first and second rounded corners is a convexly curved corner, and wherein the insulating and elastomeric sealing sleeve has first and second rounded corners which are in abutment with and cover to seal the first and second rounded corners.

12. The ECG electrode of claim 11, wherein the peripheral flange has a second end portion which is distal from the signal transmission pad and which comprises a third rounded corner and a fourth rounded corner, wherein each of the third and fourth rounded corners is a convexly curved corner, and wherein the insulating and elastomeric sealing sleeve has third and fourth rounded corners which are in abutment with and cover to seal the third and fourth rounded corners.

13. The ECG electrode of claim 1, wherein the conductive elastomeric electrode body is made of a conductive customer selected from a group consisting of carbonized elastomer, carbonized rubber, carbonized silicone rubber, and carbonized thermoplastics.

14. The ECG electrode of claim 13, wherein the insulating and elastomeric sealing sleeve is an impermeable sleeve which is made of an electrically insulating and water-impervious elastomer, and wherein the insulating and elastomeric sealing sleeve is over-molded onto the signal collection pad and the signal transmission pad to form a watertight seal to seal the signal collection pad and the signal transmission pad, leaving only the signal collection surface exposed for skin contact.

15. The ECG electrode of claim 14, wherein the insulating and elastomeric sealing sleeve is made of an electrically insulating material selected from a group consisting of rubber, silicone rubber, and thermoplastics.

16. A heart rate monitoring chest strap for collecting ECG signals in sea or chlorinated water, comprising a pair of ECG signal collection electrodes mounted on a strap,
wherein each electrode comprises an elongate and conductive and elastomeric electrode body on which a first portion, a second portion, and a third portion interconnecting the first portion and the second portion are defined;
wherein the first portion comprises a signal collection portion including a signal collection pad, the second portion comprises a signal output portion including a signal output pad, and the third portion comprises a signal transmission portion including a signal transmission pad for transmitting ECG signals collected by the signal collection portion to the signal output portion;
wherein a signal output terminal for outputting collected ECG signals is disposed on the signal output portion;
the signal collection portion defines a signal collection surface and a peripheral surrounding the signal collection surface, the signal collection surface protruding above the peripheral portion;
wherein an insulating and elastomeric sealing sleeve is integrally moulded on the conductive elastomeric electrode body to cover the first portion, the second portion and the third portion, leaving the signal collection surface and the signal output terminal un-covered;
wherein the conductive elastomeric electrode body has a resistance of 400 ohm or less, the resistance being measured between the signal collection surface and the signal output terminal, and a width ratio of the signal transmission pad to the signal collection surface is between 0.6 to 0.25; wherein the heart rate monitoring chest strap is adapted to collect ECG signals when worn by a user and immersed in sea or chlorinated water.

17. The chest strap of claim 16, wherein the insulating and elastomeric sealing sleeve is made of an electrically insulating material selected from a group consisting of rubber, silicone rubber, and thermoplastics.

18. The chest strap of claim 17, wherein the conductive elastomeric electrode body is made of a conductive elastomer selected from a group consisting of carbonized elastomer, carbonized rubber, carbonized silicone rubber, and carbonized thermoplastics.

19. The chest strap of claim 18, wherein the insulating and elastomeric sealing sleeve is an impermeable sleeve which is made of an electrically insulating and water-impervious elastomer, and wherein the insulating and elastomeric sealing sleeve is over-molded onto the signal collection pad and the signal transmission pad to form a watertight seal to seal the signal collection pad and the signal transmission pad, leaving only the signal collection surface exposed for skin contact.

20. The chest strap of claim 18, wherein the insulating and elastomeric sealing sleeve and the conductive elastomeric electrode body are made of the same elastomer.

* * * * *